(12) United States Patent
Baid

(10) Patent No.: US 10,751,512 B2
(45) Date of Patent: Aug. 25, 2020

(54) INTRAVENOUS (IV) CATHETER APPARATUS

(71) Applicant: POLY MEDICURE LIMITED, Haryana (IN)

(72) Inventor: Rishi Baid, New Dehli (IN)

(73) Assignee: POLY MEDICURE LIMITED, Haryana, IN (US)

( * ) Notice: Subject to any disclaimer, the term of this patent is extended or adjusted under 35 U.S.C. 154(b) by 174 days.

(21) Appl. No.: 15/029,996

(22) PCT Filed: Oct. 13, 2014

(86) PCT No.: PCT/IB2014/065260
§ 371 (c)(1),
(2) Date: Apr. 15, 2016

(87) PCT Pub. No.: WO2015/056148
PCT Pub. Date: Apr. 23, 2015

(65) Prior Publication Data
US 2016/0235949 A1 Aug. 18, 2016

(30) Foreign Application Priority Data
Oct. 17, 2013 (IN) .......................... 3088/DEL/2013

(51) Int. Cl.
*A61M 25/06* (2006.01)
*A61M 5/32* (2006.01)
*A61M 5/162* (2006.01)

(52) U.S. Cl.
CPC ...... *A61M 25/0618* (2013.01); *A61M 5/1626* (2013.01); *A61M 5/3273* (2013.01);
(Continued)

(58) Field of Classification Search
CPC ........ A61M 25/0618; A61M 2005/325; A61M 5/1626; A61M 5/3273; A61M 5/3291; A61M 25/0606; A61M 2005/3247
See application file for complete search history.

(56) References Cited

U.S. PATENT DOCUMENTS 5,246,426 A * 9/1993 Lewis ............... A61M 25/0693
604/168.01
5,306,253 A 4/1994 Brimhall et al.
(Continued)

FOREIGN PATENT DOCUMENTS

WO 2012076990 A1 6/2012
WO 2013124765 A1 8/2013

OTHER PUBLICATIONS

International Search Report and Written Opinion for PCT/IB2014/065260 dated Feb. 16, 2015.

*Primary Examiner* — Manuel A Mendez
*Assistant Examiner* — Courtney B Frederickson
(74) *Attorney, Agent, or Firm* — Moore & Van Allen PLLC; Henry B. Ward, III

(57) ABSTRACT

An intravenous (IV)catheter apparatus comprising: a tubular catheter (10) having a proximal end (50) and a distal end (16) mounted to a catheter hub (40); a needle (12) defining an axial direction (A) having a needle shaft (22) with a needle tip (14) at a distal end (16) and a needle hub mounted to the proximal end (50) of the needle shaft (22); a needle guard (30) arranged movably on the needle shaft (22), wherein said needle shaft (22) extends through said tubular catheter (10) such that said needle tip (14) of said needle (12) protrudes from said distal end (16) of said tubular catheter (10); and wherein said needle shaft (22) is provided with: an engagement means (26) adapted to engage with the said needle guard (30) in order to prevent said needle guard (Continued)

(30) from sliding off said needle tip (14); and one or more lateral openings (28) covered by said tubular catheter (10).

10 Claims, 7 Drawing Sheets

(52) U.S. Cl.
CPC ...... *A61M 5/3291* (2013.01); *A61M 25/0606* (2013.01); *A61M 25/0693* (2013.01); *A61M 2005/325* (2013.01); *A61M 2005/3247* (2013.01)

(56) References Cited

U.S. PATENT DOCUMENTS

| | | | | |
|---|---|---|---|---|
| 6,280,424 | B1* | 8/2001 | Chang | A61M 25/06 |
| | | | | 604/272 |
| 6,914,212 | B2* | 7/2005 | Adams | A61M 5/3273 |
| | | | | 219/121.6 |
| 7,604,616 | B2* | 10/2009 | Thoresen | A61M 5/3273 |
| | | | | 604/164.08 |
| 8,439,877 | B2* | 5/2013 | Burkholz | A61M 5/329 |
| | | | | 604/110 |
| 8,641,675 | B2* | 2/2014 | Stout | A61M 25/0606 |
| | | | | 604/167.01 |
| 2010/0305519 | A1* | 12/2010 | McKinnon | A61M 25/0105 |
| | | | | 604/272 |
| 2012/0041371 | A1* | 2/2012 | Tal | A61M 25/0606 |
| | | | | 604/164.08 |
| 2012/0078200 | A1 | 3/2012 | Woehr et al. | |
| 2012/0232500 | A1* | 9/2012 | Baid | A61M 25/0618 |
| | | | | 604/263 |
| 2013/0066276 | A1 | 3/2013 | Ito et al. | |

\* cited by examiner

INTRAVENOUS (IV) CATHETER APPARATUS

CROSS-REFERENCE TO THE RELATED APPLICATION

This application claims priority from Indian Patent Application No. 3088/DEL/2013 dated Oct. 17, 2013, the entire disclosure of which is incorporated herein by reference.

FIELD OF THE INVENTION

The invention relates to an intravenous (IV) catheter apparatus comprising a tubular catheter having a proximal end and a distal end, a needle defining an axial direction and having a needle shaft and a needle tip at a distal end of the needle shaft, wherein the needle shaft extends through the catheter such that the needle tip protrudes from the distal end of the tubular catheter, and wherein the needle shaft comprises an engagement means adapted to engage with a needle guard slidably arranged on the needle shaft in order to prevent the needle guard from sliding off the needle tip.

BACKGROUND OF THE INVENTION

An intravenous (IV) catheter apparatus of this kind is generally known and, for example, used to administer medicine to a patient or to take blood from a patient.

In use, the tubular catheter is inserted into a blood vessel of the patient, typically a vein, by means of the needle which will be withdrawn from the catheter after insertion of the tubular catheter into the blood vessel. When the needle tip enters the blood vessel, blood flows through a lumen of the needle into a needle hub provided at a proximal end of the needle, where it can be observed by the person handling the catheter apparatus. The event of blood entering the needle hub is called blood flashback and is used by the person handling the catheter apparatus to confirm venipuncture, from which point on the person inserts the catheter as far as desired under a decreased inclination of the needle in order to not puncture the back wall of the blood vessel.

In the case of delayed blood flashback there is a risk that the person handling the catheter apparatus continues to push the needle into the blood vessel under the increased original inclination of the needle until it exits at the rear side of the blood vessel. This second venipuncture represents a risk to the health of the patient as it may result in inner bleeding. Apart from that the catheter apparatus will have to be removed and replaced by a new one, i.e. the process of introducing the catheter will have to be repeated which is unpleasant and painful to the patient.

SUMMARY OF THE INVENTION

It is an object of the invention to provide an intravenous (IV) catheter apparatus which allows for safer and more reliable placement of the catheter in the patient's blood vessel.

This object is satisfied by an intravenous (IV) catheter apparatus comprising: a tubular catheter having a proximal end and a distal end mounted to a catheter hub; a needle defining an axial direction having a needle shaft with a needle tip at a distal end and a needle hub mounted to the proximal end of the needle shaft; and a needle guard arranged movably on the needle shaft, wherein said needle shaft extends through said tubular catheter such that said needle tip of said needle protrudes from said distal end of said tubular catheter, and wherein said needle shaft is provided with an engagement means adapted to engage with the said needle guard in order to prevent said needle guard from sliding off said needle tip, and at least one lateral opening covered by said tubular catheter.

The at least one lateral opening provides communication between a lumen of the needle and an interior of the tubular catheter. In the event of first venipuncture blood entering the lumen of the needle can exit the needle through the lateral opening and thus become visible for the person handling. The at least one lateral opening is preferably large enough in order to provide an early blood flashback function within the tubular catheter such that the practitioner can recognize that he has placed the needle correctly within a patient's vein. In case of a correct positioning of the needle, blood pours out of the opening within the needle shaft into the space between the needle shaft and the inner wall of the transparent tubular catheter and is visible to the practitioner. Preferably, the at least one lateral opening is positioned close to the needle tip so that the blood does not have to travel the length of the needle to enter the needle hub in order to become visible. Instead, blood entering the lumen of the needle upon venipuncture partly exits the needle again near the needle tip, thereby becoming particularly quickly and, thus, allowing for particularly fast venipuncture confirmation.

The needle guard may comprise a base portion having a needle passage extending in an axial direction from a proximal side of the base portion through the base portion to a distal side of the base portion; first and second arms extending substantially in the axial direction from the distal side of the base portion; and a distal wall which is transversely arranged at a distal region of the first arm.

Furthermore, the needle guard may include a stopping element which is arranged in the needle guard, in particular, which is received in a recess provided in the needle guard for stopping movement of the needle shaft relative to the said needle guard. The stopping element may be made of a material different from the material of the base portion and has a through-bore with a profile which is adapted to the principal outer profile of the needle shaft. In the case of e.g. circular cross-sections, a diameter of the through-bore can be slightly larger than a principal outer diameter of the needle. The stopping element may be formed by a washer integrally formed within the base portion.

In order to allow a trouble free movement of the needle relative to the needle guard when the needle is withdrawn from the tubular catheter, the lateral opening is preferably arranged on the needle shaft such that it does not come into the path of the first and second arms of the needle guard in the axial direction. In particular, the lateral opening is arranged on the needle shaft such that it does not come into the path in the axial direction of the distal wall of the first arm when the needle is withdrawn from the tubular catheter. This arrangement ensures that the first and second arm of the needle guard do not get stuck or engage with the lateral opening when the needle is withdrawn from the tubular catheter. In particular, this arrangement ensures that distal wall of the first arm does not get stuck or engages with the lateral opening when the needle is withdrawn from the tubular catheter.

According to a preferred embodiment of the invention, the engagement means is arranged between the at least one lateral opening and the needle tip.

An arrangement of the engagement means between the at least one lateral opening and the needle tip is particularly advantageous if the profile forming the inner diameter of the tubular catheter decreases in the axial direction, thus forming a tapered distal end of the tubular catheter which tightly surrounds the needle shaft. If the lateral opening were covered by the tapered distal end of the tubular catheter in this case, there would be a risk that the tapered distal end of the tubular catheter may hinder and/or obstruct the flow of blood from entering the gap between the needle shaft and the tubular catheter. Accordingly, the arrangement of the at least one lateral opening proximally from the engagement means ensures that the blood entering the gap between the needle shaft and the tubular catheter easily spreads in the gap due to capillary action and can be seen through the transparent material of the tubular catheter, thereby allowing prompt confirmation of successful venipuncture without being hindered and/or obstructed by the tapered distal end of the tubular catheter. In other words, in order to allow the flow of blood from the lateral opening pursuant to the venipuncture, the lateral opening may preferably be arranged away from the tapered distal end of the tubular catheter in a direction opposite to the axial direction.

It is to be noted that even if the engagement means is arranged between the lateral opening and the needle tip, the blood does not have to travel the length of the needle to enter the needle hub in order to become visible. Instead, in this arrangement blood entering the lumen of the needle upon venipuncture passes the engagement means and partly exits the needle through the lateral opening, thereby becoming visible particularly quickly and, thus, allowing for particularly fast venipuncture confirmation.

As a result, the intravenous catheter apparatus allows faster and more reliable confirmation of successful venipuncture which makes the handling of the catheter apparatus easier both for the person placing it and the patient on whom it is used.

Additionally or alternatively to an arrangement of the engagement means between the at least one lateral opening and the needle tip, at least one lateral opening may be arranged between the engagement means and the needle tip. A lateral opening may, thus, be arranged proximal and/or distal to the engagement means, i.e. the arrangement of the engagement means and lateral opening may be interchanged.

If a lateral opening is arranged between the engagement means and the needle tip, the blood does not have to pass the engagement means to become visible in the needle hub. Hence, the time at which blood entering the needle upon venipuncture becomes visible to the person handing the catheter apparatus, is independent of the design of the engagement means. Hence, even if the engagement means is designed such that it would normally slow down the flow of blood through the needle and, thus, delay blood flashback, it does not have any adverse effect on the timing of venipuncture confirmation in the apparatus of the invention.

According to a further embodiment, more than one lateral opening may be provided on the needle shaft. With relation to the engagement means, such openings may be arranged proximal and/or distal to the engagement means.

According to a further embodiment, the needle shaft may comprise a lateral opening that is not covered by the tubular catheter.

In order to improve the visibility of the blood exiting the needle through the lateral opening, the tubular catheter advantageously comprises a transparent material.

According to a preferred embodiment, the at least one lateral opening comprises a slit which is cut into the needle shaft and which may have a length in the range of 0.3 to 1 mm. This slit can extend either in the axial direction or in a direction transverse thereto. Such a slit is easy to manufacture and thus helps to minimize manufacturing costs of the catheter apparatus. Those skilled in the art will appreciate that various other shapes of the lateral opening are likewise suitable. For example, the shape of the lateral opening may be of any geometrical shape such as curve, square, rectangular, circular, semi-circular, and combinations thereof and/ or the like shapes. In further embodiments, the lateral opening may comprise an opening such as a hole, groove, puncture, cavity, perforation or the like.

According to a further embodiment, at least two discrete lateral openings may be arranged along the circumference of the needle shaft seen in a direction transverse to the axial direction. Additionally or alternatively, at least two discrete lateral openings may be arranged along the length of the needle shaft seen in the axial direction.

In order to enhance spreading of the blood exiting the needle through the lateral opening inside the tubular catheter, an outer diameter of the needle shaft may be slightly smaller than an inner diameter of the tubular catheter. The profile forming the inner diameter of the tubular catheter may decrease in the axial direction forming a tapered distal end. The enhanced spreading of the blood improves visibility of the blood through the tubular catheter and, thus, makes detection of successful venipuncture faster and more reliable.

In order to make the insertion of the tubular catheter into a patient's blood vessel even more agreeable, the tubular catheter may slightly tapered in its distal end region such that the distal end of the tubular catheter tightly surrounds the needle shaft.

According to one embodiment the engagement means comprises an enlargement of the needle shaft in at least one direction transverse to the axial direction. The enlargement may be provided between the distal end and the proximal end of the needle shaft.

In a preferred embodiment, the enlargement may be made by a crimping of the needle shaft. However, other ways of forming the enlargement are possible, such as applying additional material to the needle shaft, e.g. by soldering, welding or gluing, or the like etc.

The inner profile of the needle can either be reduced in the region of the enlargement, for example, if the enlargement is formed by crimping, or it can be substantially constant throughout the length of the needle, for example, if the enlargement is formed by applying additional material to the needle shaft.

Thus, an engagement means that is particularly easy to manufacture comprises a crimped portion of the needle shaft. The manufacturing costs of the needle thus can be further reduced.

Prior to the use of the catheter apparatus, the needle guard is arranged in the catheter hub near a proximal end of the needle shaft. In this situation, the needle extends completely through the needle guard, thereby deflecting the first arm of the needle guard outwards, i.e. at an angle to the axial direction, such that the distal wall of the first arm is supported on the needle shaft. Following the insertion of the catheter into a patient, the needle is withdrawn from the tubular catheter and the needle shaft moves through the needle guard while the needle guard is retained in the catheter hub. Once the needle tip passes the transverse distal wall of the needle guard, i.e. such that the needle shaft no longer supports the distal wall, a restoring force ensures that the first arm of the needle guard is moved back into alignment with the axial direction of the needle guard, so that the needle tip is blocked by the distal wall of the needle guard, i.e. the needle tip is prevented from axially projecting out of the needle guard.

Once the needle tip is blocked by the distal wall and the needle is being further retracted, the engagement means of the needle shaft may engage with the stopping element to prevent the needle guard from being removed from the needle shaft. If the stopping element is made from a material which is harder and less easily distorted than the material of the base portion, the needle guard is secured more effectively on the needle shaft and can be retained even if excessive external force is applied when pulling on the needle, as the engagement means is prevented from being pulled through the base portion of the needle guard due to the stopping element. Hence, it is prevented that the needle guard is removed from the needle tip accidentally and, as a result, the needle guard provides a better protection against accidental pricking and thus increased safety for the person handling the catheter apparatus.

In a further embodiment of the needle guard, a tension element surrounds the first and second arms of the needle guard. In the deflected state of the first arm, the tension element is expanded against a restoring force of the tension element. Once the needle shaft no longer supports the distal wall of the first arm, the tension element aids the repositioning of the first arm back into axial alignment with the axial direction. This repositioning is necessary so that the distal wall can block the needle tip from axially sliding out of the needle guard. In addition, the tension element helps to enclose a space between the first and second arms and thus helps to prevent the needle shaft and the needle tip from projecting sideways out of the needle guard. In other words, the tension element adds to the protective effect of the needle guard.

According to a further embodiment the invention, the two arms of the needle guard, in particular the first arm having the distal wall blocking the needle tip, may have a recess in order to provide a high strength and a spring-like action of the first arm such that it is biased into the blocking position with its distal wall in front of the needle tip.

In a further embodiment of the needle guard, a groove may be provided in a side of the distal wall, with the groove extending substantially in the axial direction. The groove may act as a guide groove for the needle shaft and may aid the axial movement of the needle shaft relative to the needle guard. Due to the groove, the needle shaft is prevented from sliding sideways off the distal wall. Such a sideways movement would significantly increase the force required to move the needle shaft relative to the needle guard, which would prevent a correct functioning of the needle guard.

According to a further embodiment of the invention, the catheter hub within which the needle guard is received in a ready position, includes holding means for holding the needle guard even under retracting forces acting on the needle guard when the needle is retracted out of the patient's vein. These holding means may include a recess formed on the inner circumferential surface of the catheter hub into which a projection formed on the first arm of the needle guard securely engages in the ready position, i.e. when the first arm is deflected and spread apart from the second arm by the needle shaft. Alternatively, these holding means may include a bump formed on the inner circumferential surface of the catheter hub. The holding means on the inner circumferential surface of the catheter hub maybe also formed by a combination of a recess and a bump wherein the needle guard has a corresponding complimentary profile of a projection engaging the recess on the inner circumferential surface of the catheter hub and a recess engaging with the bump on the inner circumferential surface of the catheter hub.

As an alternative, the holding means may include at least one outer arm formed on the base portion and adapted to engage the catheter hub on its outer circumferential surface. In particular the holding means may include two outer arms formed on substantially diametrical locations of the base portion and adapted to engage the catheter hub on its outer circumferential surface. By providing such holding means, the holding function is alternatively or additionally provided at the outside of the catheter hub. Thereby, the manufacturing effort can be reduced and the safety in operation may be further increased.

In a further embodiment, the catheter hub may have an opening or window in order to provide additional space for the deflected first arm in the ready position. The opening or window can be formed as a through-hole through the circumferential wall of the catheter hub. The opening in the circumferential wall of the catheter hub may also provide a holding edge acting as the holding means for holding the needle guard within the catheter hub in the ready position even under retracting forces applied on the needle by the practitioner.

Further advantageous embodiments of the invention and preferred apparatuses for carrying out the invention are described in connection with the accompanying drawings.

BRIEF DESCRIPTION OF THE ACCOMPANYING DRAWINGS

The embodiments of the invention are described in the following description and in the accompanying drawings, wherein.

DETAILED DESCRIPTION OF THE INVENTION

Generally speaking, the term proximal refers to a region of the device or a location on the device which is closest to, for example, a clinician using the device. In contrast to this, the term distal refers to a region of the device which is farthest from the clinician, for example, the distal region of a needle will be the region of a needle containing the needle tip which is to be inserted e.g. into a patient's vein.

Figure 1:
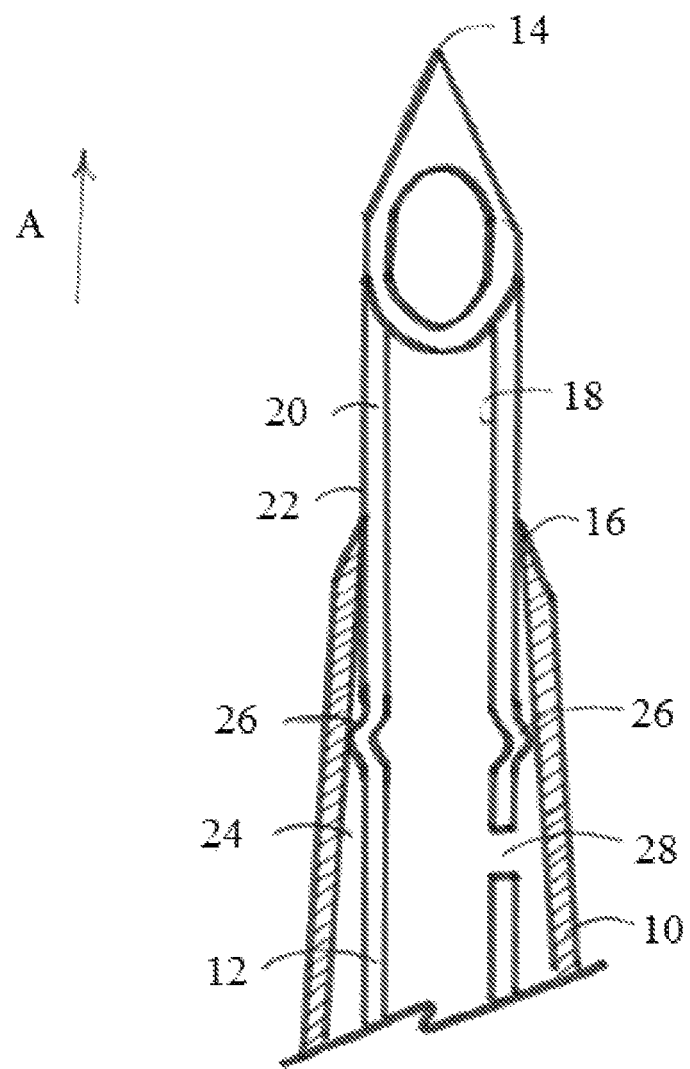
FIG. 1 shows a longitudinal sectional view of a distal end region of an intravenous (IV) catheter apparatus in accordance with one embodiment of the invention.

FIG. 1 shows a distal end portion of a tubular catheter 10 of an intravenous (IV) catheter apparatus of the invention. The tubular catheter 10 is made of a transparent material, for example, a transparent plastic material.

A needle 12 defining an axial direction (A) extends through the tubular catheter 10 such that a distal tip of the needle 12 protrudes from a distal end 16 of the tubular catheter 10. The needle 12 has a lumen 18 which extends along the length of the needle 12 in the axial direction (A) and is defined by a wall 20 of the needle 12. The needle wall 20 forms a needle shaft 22.

The outer diameter of the needle shaft 22 is slightly smaller than the inner diameter of the tubular catheter 10 in order to provide a small gap 24 between the needle shaft 22. In its distal end region of the tubular catheter 10 is slightly tapered such that the distal end 16 of the tubular catheter 10 tightly surrounds the needle shaft 22.

Figure 7:
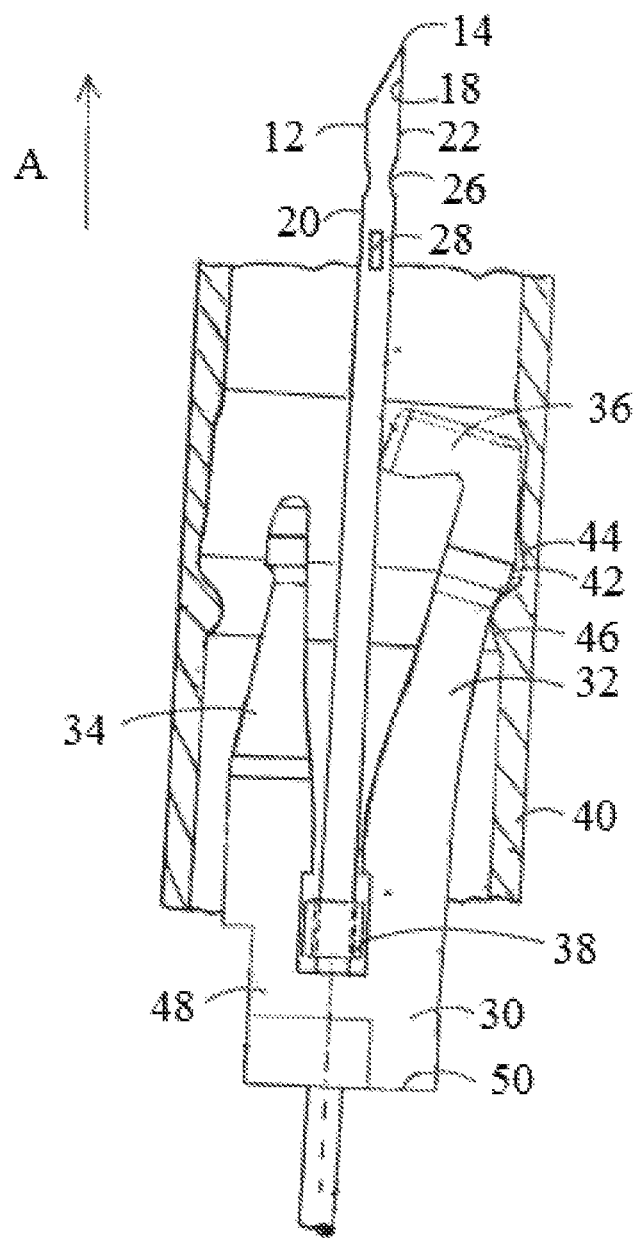
FIG. 7 shows a longitudinal sectional view of a part of an intravenous (IV) catheter apparatus with a needle guard movably arranged on the needle in accordance with one of the embodiments of the invention.

Proximal from the needle tip 14 the needle shaft 22 is provided with an engagement means 26 for preventing a needle guard 30 as shown in FIG. 7 slidably arranged on the needle shaft 22 from moving beyond the needle tip 14. The engagement means 26 may comprise any form of irregularity of the needle shaft 22, for example, an enlargement of the outer profile of the needle shaft 22 at least in one direction transverse to the axial direction (A).

In the illustrated embodiment, the engagement means 26 comprises a crimped portion of the needle shaft 22.

The needle guard 30 may comprise a generally cylindrical base portion 48 made of a plastic material and having an axial bore through which the needle 12 extends. The inner diameter of the bore is adapted to the principal outer diameter of the needle shaft 22 such that the needle shaft 22 is free to slide through the bore, but the engagement means 26 of the needle 12 cannot pass the base portion 48 of the needle guard 30 due to the stopping element 38 provided therein.

The needle guard 30 further comprise first 32 and second 34 arms extending generally in the axial direction (A) from the distal side of the base portion 48 and a distal wall 36 which is transversely arranged at a distal region of the first arm 32. At least one of the arms 32, 34 has elastic properties such that it can be deflected slightly off the axial direction (A) by the needle shaft 22. Both of the first 32 and second 34 arms may be integrally formed with the base portion 48. Alternatively, one of the arms 32, 34 may be integral with the base portion 48 whereas the other one of the arms 32, 34 may be made of a strip of sheet metal.

The length of the first arm 32 is longer than the distance between the needle tip 14 and the engagement means 26, such that the distal wall 36 of the first arm 32 can move in front of the needle tip 14 and capture the needle tip 14 in the needle guard 30 before the engagement means 26 of the needle 12 engages with the base portion 48 of the needle guard, in particular with the stopping element 38 provided therein.

Preferably, the first 32 and second 34 arms are surrounded by an elastic element which biases the first 32 and second 34 arms towards the needle 12. The elastic element may cover a substantial portion of the first 32 and second 34 arms seen in the axial direction (A) and, thus, prevent the needle tip 14 captured between the arms 32, 34 from protruding sideway out of the needle guard 30.

The engagement means 26 is provided in the needle wall 20 in a region between the needle tip 14 and at least one lateral opening 28. The lateral opening 28 is positioned such that it is covered by the tubular catheter 10 when the needle tip 14 protrudes from the distal end 16 of the tubular catheter 10, i.e. it is arranged proximal to the engagement means 26. The lateral opening 28 thus provides communication between the lumen 18 of the needle 12 and the interior of the tubular catheter 10.

When the needle 12 together with the tubular catheter 10 is inserted into a blood vessel of a patient, blood flows into the lumen 18 of the needle 12 in the event of venipuncture. The blood flowing into the lumen 18 of the needle 12 partly exits the needle 12 through the lateral opening 28 and enters the gap 24 between the needle shaft 22 and the tubular catheter 10. The blood entering the gap 24 between the needle shaft 22 and the tubular catheter 10 spreads in the gap 24 due to capillary action and can be seen through the transparent material of the tubular catheter 10, thereby allowing prompt confirmation of successful venipuncture.

Figure 2:
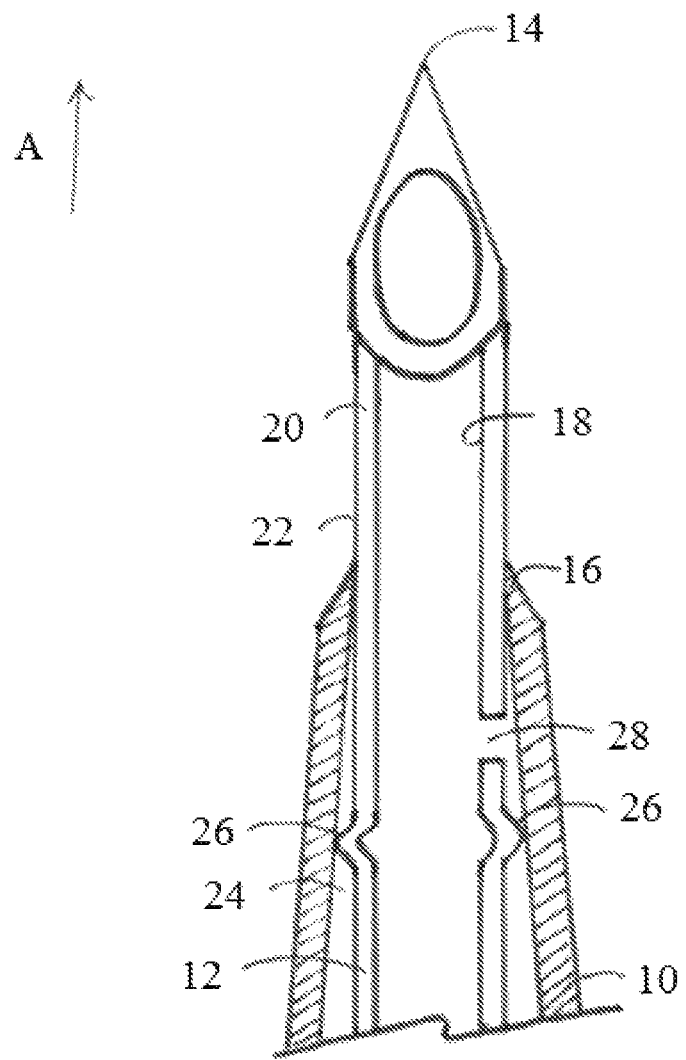
FIG. 2 shows a longitudinal sectional view of a distal end region of an intravenous (IV) catheter apparatus in accordance with another embodiment of the invention.

FIG. 2 shows a distal end portion of a tubular catheter of an intravenous (IV) catheter apparatus according to another embodiment of the invention, wherein at least one lateral opening 28 is provided in the needle wall 20 in a region between the needle tip 14 and the engagement means 26. The lateral opening 28 is positioned such that it is covered by the tubular catheter 10 when the needle tip 14 protrudes from the distal end 16 of the tubular catheter 10, i.e. it is arranged between the engagement means 26 and the distal end 16 of the tubular catheter 10. The lateral opening 28 thus provides communication between the lumen 18 of the needle 12 and the interior of the tubular catheter 10.

Figure 3:
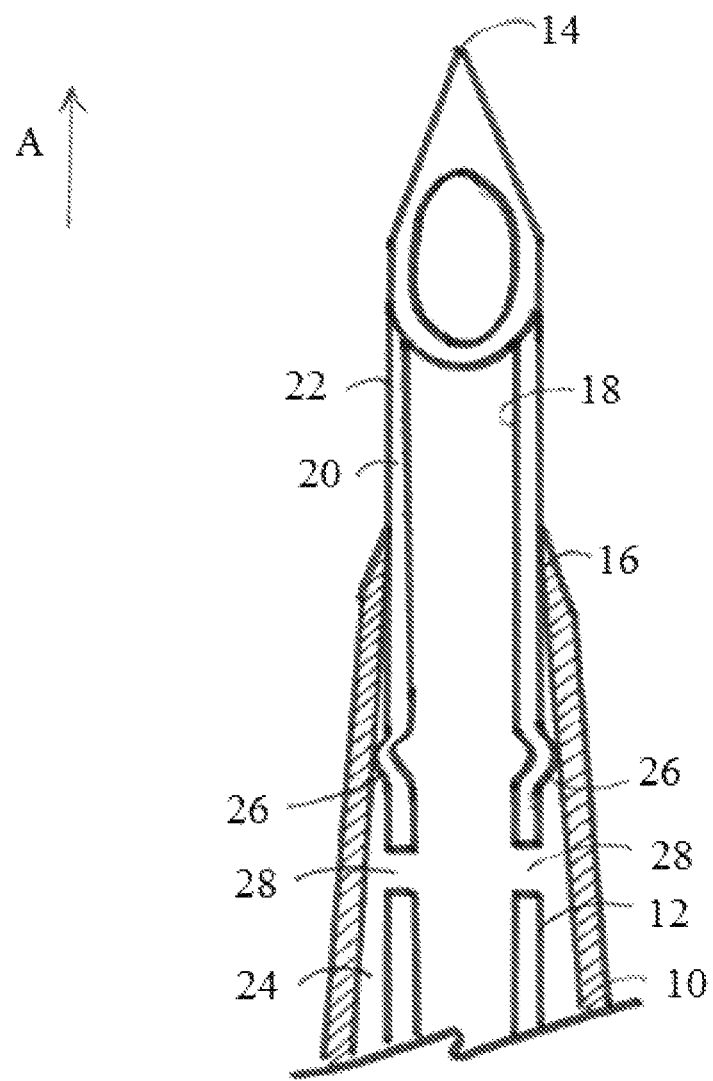
FIG. 3 shows a longitudinal sectional view of a distal end region of an intravenous (IV) catheter apparatus in accordance with another embodiment of the invention.

FIG. 3 shows a distal end portion of the tubular catheter of an intravenous (IV) catheter apparatus according to another embodiment of the invention, the engagement means 26 is provided in the needle wall 20 in a region between the needle tip 14 and lateral opening 28. As shown, more than one lateral openings 28 are provided on the needle wall 20. The lateral openings 28 are positioned such that they are covered by the tubular catheter 10 when the needle tip 14 protrudes from the distal end 16 of the tubular catheter 10, i.e. the lateral openings 28 are arranged proximal to the engagement means 26. The lateral openings 28 thus provide communication between the lumen 18 of the needle 12 and the interior of the tubular catheter 10.

Figure 4:
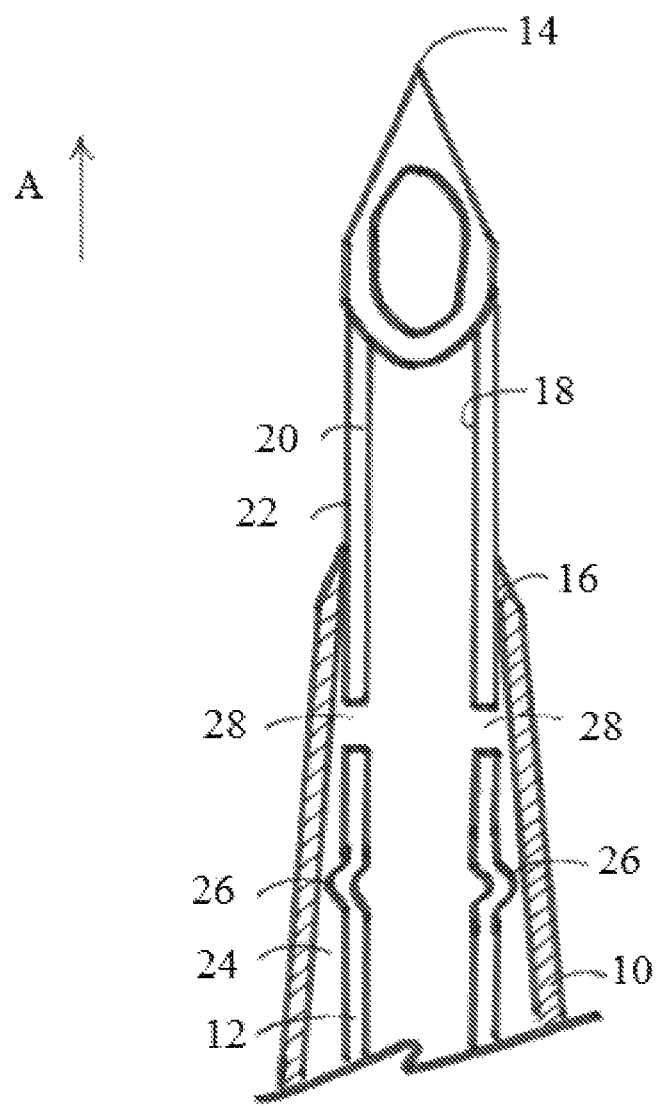
FIG. 4 shows a longitudinal sectional view of a distal end region of an intravenous (IV) catheter apparatus in accordance with another embodiment of the invention.

FIG. 4 shows a distal end portion of a tubular catheter of an intravenous (IV) catheter apparatus according to another embodiment of the invention, wherein more than one lateral openings 28 are provided in the needle wall 20 in a region between the needle tip 14 and the engagement means 26. The lateral openings 28 are positioned such that they are covered by the tubular catheter 10 when the needle tip 14 protrudes from the distal end 16 of the tubular catheter 10, i.e. the lateral openings are arranged between the engagement means 26 and the distal end 16 of the tubular catheter 10. The lateral openings 28 thus provide communication between the lumen 18 of the needle 12 and the interior of the tubular catheter 10.

Figure 5:
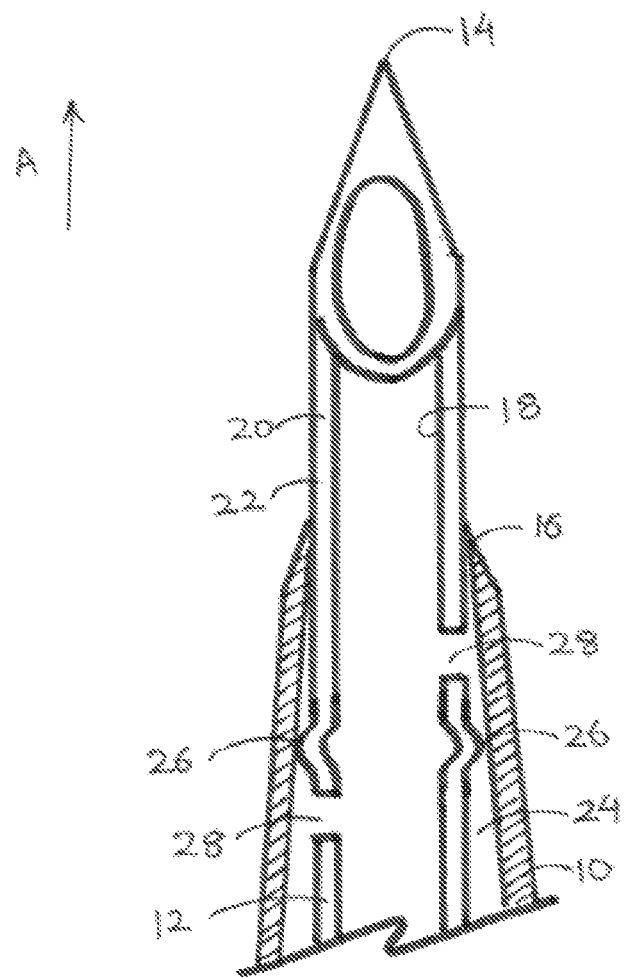
FIG. 5 shows a longitudinal sectional view of a distal end region of an intravenous (IV) catheter apparatus in accordance with another embodiment of the invention.
Figure 6:
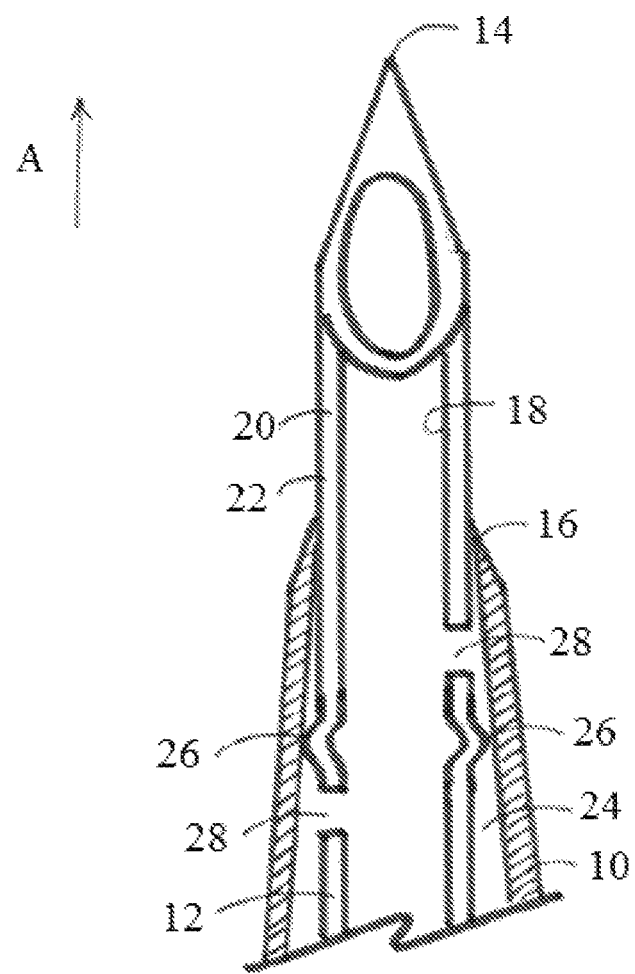
FIG. 6 shows a longitudinal sectional view of a distal end region of an intravenous (IV) catheter apparatus in accordance with another embodiment of the invention.

FIGS. 5 and 6 shows a distal end portion of a tubular catheter of an intravenous (IV) catheter apparatus according to further embodiments of the invention, wherein more than one lateral openings 28 are provided in the needle wall 20. As shown lateral openings 28 are provided proximal and distal to the engagement means 26. The lateral openings 28 are positioned such that they are covered by the tubular catheter 10 when the needle tip 14 protrudes from the distal end 16 of the tubular catheter 10. The lateral openings 28 thus provide communication between the lumen 18 of the needle 12 and the interior of the tubular catheter 10.

FIG. 7 shows a longitudinal sectional view of a part of an intravenous (IV) catheter apparatus with a needle guard movably arranged on the needle in accordance with one of the embodiments of the invention. As mentioned above, prior to the use of the catheter apparatus the needle 12 extends through the tubular catheter 10 and the needle guard 30 is arranged in the catheter hub 40. In this situation, the distal wall 36 of the needle guard 30 contacts the needle 12, with the needle shaft 22 being guided in the groove (not shown) in the side of the distal wall 36. The needle shaft 22 thereby supports the distal wall 36, due to which the first arm 32 of the needle guard 30 is deflected outwards, i.e. away from the needle 12, against a restoring force of the tension element (not shown).

In order to retain the needle guard 30 in the catheter hub 40 while the needle 12 is being withdrawn from the tubular catheter 10, the shoulders 42 provided on both the first arm 32 and the second arm 34 of the needle guard 30 engage with recesses 44 or protrusions 46 or combinations thereof provided on the inner circumferential surface of the catheter hub 40. The protrusions 46 may form an annular ring extending along the entire inner periphery of the catheter hub 40, or they may form one or more ring segments extending along only a respective part of the inner periphery of the catheter hub 40. Similarly, the recesses 44 may form an annular groove extending along the entire inner periphery of the catheter hub 40, or they may form one or more groove segments extending along only a respective part of the inner periphery of the catheter hub 40.

The engagement means 26 is provided in the needle wall 20 in a region between the needle tip 14 and at least one lateral opening 28. The lateral opening 28 is positioned such that it is covered by the tubular catheter 10 when the needle tip 14 protrudes from the distal end 16 of the tubular catheter 10, i.e. it is arranged proximal to the engagement means 26. For the sake clarity, this embodiment illustrates the catheter apparatus without the tubular catheter 10. The lateral opening 28 thus provides communication between the lumen 18 of the needle 12 and the interior of the tubular catheter 10.

As shown and in order to allow a trouble free movement of the needle 12 relative to the needle guard 30, the lateral opening 28 is arranged on the needle shaft 22 such that it does not come into the path of the first 32 and second 34 arms of the needle guard 30 in the axial direction (A). In particular, the lateral opening 28 is arranged on the needle shaft 22 such that it does not come into the path in the axial direction (A) of the distal wall 36 of the first arm 32 when the needle 12 is withdrawn from the tubular catheter 10. This arrangement ensures that the first 32 and second 34 arm of the needle guard 30 do not get stuck or engage with the lateral opening 28 when the needle 12 is withdrawn from the tubular catheter 10. In particular, this arrangement ensures that distal wall 36 of the first arm 32 does not get stuck or engages with the lateral opening 28 when the needle 12 is withdrawn from the tubular catheter 10.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the spirit or scope of the invention as set forth herein.

Accordingly, it is not intended that the scope of the foregoing description be limited to the exact description set forth above, but rather that such description be construed as encompassing all of the features that reside in the present invention, including all the features and embodiments that would be treated as equivalents thereof by those skilled in the relevant art.

LIST OF REFERENCE NUMERAL

10 tubular catheter
12 needle
14 needle tip
16 distal end
18 lumen
20 needle wall
22 needle shaft
24 gap
26 engagement means
28 lateral opening
30 needle guard
32 first arm
34 second arm
36 distal wall
38 stopping element
40 catheter hub
42 shoulders
44 recess
46 protrusion
48 base portion
50 proximal end
52 proximal side
54 distal side
A axial direction

I claim:

1. An intravenous (IV) catheter apparatus comprising:
a tubular catheter having a proximal end and a distal end mounted to a catheter hub;
a needle defining an axial direction (A) having a needle shaft with a needle tip at a distal end; and
a needle guard arranged movably on the needle shaft;
wherein said needle shaft extends through said tubular catheter such that said needle tip of said needle protrudes from said distal end of said tubular catheter;
wherein said needle shaft is provided with:
an engagement means adapted to engage with said needle guard in order to prevent said needle guard from sliding off said needle tip;
at least two lateral openings arranged along the circumference of the needle shaft in a direction transverse to said axial direction and covered by said tubular catheter,
wherein each of the at least two lateral openings comprise a slit defining a longitudinal slit axis and wherein the longitudinal slit axis extends in a direction transverse to the axial direction (A) of the needle,
wherein the at least two lateral openings comprise a first lateral opening arranged proximal to the engagement means and a second lateral opening arranged distal to said engagement means,
wherein said first and second lateral openings are arranged on opposite sides of the needle shaft, and
wherein the needle guard comprises a first arm and a second arm and wherein at least one lateral opening is arranged on needle shaft out of a path of the first and second arms of the needle guard in the axial direction (A) when the needle is retracted.

2. The intravenous (IV) catheter apparatus in accordance with claim 1, wherein said at least two lateral openings provide communication between a lumen of said needle and an interior of said tubular catheter.

3. The intravenous (IV) catheter apparatus in accordance with claim 1, wherein an outer diameter of the needle shaft is slightly smaller than an inner diameter of said tubular catheter.

4. The intravenous (IV) catheter apparatus in accordance with claim 1, wherein said tubular catheter is slightly tapered in its distal end region such that the distal end of the tubular catheter tightly surrounds the needle shaft.

5. The intravenous (IV) catheter apparatus in accordance with claim 1, wherein said engagement means comprises an enlargement of said needle shaft in at least one direction transverse to the axial direction (A).

6. The intravenous (IV) catheter apparatus in accordance with claim 1, wherein said engagement means comprises a crimped portion of said needle shaft.

7. The intravenous (IV) catheter apparatus in accordance with claim 1, wherein said tubular catheter comprises a transparent material.

8. The intravenous (IV) catheter apparatus in accordance with claim 1, wherein said first and second lateral openings are arranged approximately 180 degrees opposite to each other along the circumference of the needle shaft.

9. The intravenous (IV) catheter apparatus in accordance with claim 1, wherein said needle guard comprises:
- a base portion having a needle passage extending in an axial direction (A) from a proximal side of the base portion through the base portion to a distal side of the base portion;
- where the first and second arms extend substantially in the axial direction (A) from the distal side of the base portion; and
- a distal wall which is transversely arranged at a distal region of the first arm.

10. The intravenous (IV) catheter apparatus in accordance with claim 1, wherein a stopping element is received in a recess provided in said needle guard for stopping movement of said needle shaft relative to said needle guard.

* * * * *